(12) United States Patent
Park et al.

(10) Patent No.: US 8,858,694 B2
(45) Date of Patent: Oct. 14, 2014

(54) ZINC OXIDE PRECURSOR CONTAINING ALKYL ZINC HALIDE AND METHOD OF DEPOSITING ZINC OXIDE-BASED THIN FILM USING THE SAME

(71) Applicant: Samsung Corning Precision Materials Co., Ltd., Gumi-si (KR)

(72) Inventors: Sooho Park, ChungCheongNam-Do (KR); Seohyun Kim, ChungCheongNam-Do (KR); Jeongwoo Park, ChungCheongNam-Do (KR); Taejung Park, ChungCheongNam-Do (KR); Young Zo Yoo, ChungCheongNam-Do (KR); GunSang Yoon, ChungCheongNam-Do (KR); Eun-Ho Choi, ChungCheongNam-Do (KR); Myong Woon Kim, ChungCheongNam-Do (KR); Bogyeong Kim, ChungCheongNam-Do (KR); Hyung Soo Shin, ChungCheongNam-Do (KR); Seung Ho Yoo, ChungCheongNam-Do (KR); Sang Do Lee, ChungCheongNam-Do (KR); Sang Ick Lee, ChungCheongNam-Do (KR); Sang Jun Yim, ChungCheongNam-Do (KR)

(73) Assignee: Samsung Corning Precision Materials Co., Ltd., Gumi-Si, Gyeongsangbuk-Do (KR)

( * ) Notice: Subject to any disclaimer, the term of this patent is extended or adjusted under 35 U.S.C. 154(b) by 0 days.

(21) Appl. No.: 13/681,108

(22) Filed: Nov. 19, 2012

(65) Prior Publication Data
US 2013/0129923 A1    May 23, 2013

(30) Foreign Application Priority Data
Nov. 17, 2011  (KR) ........................ 10-2011-0120424

(51) Int. Cl.
| | | |
|---|---|---|
| C07F 3/06 | (2006.01) |
| C03C 17/27 | (2006.01) |
| C23C 16/00 | (2006.01) |
| C23C 16/40 | (2006.01) |
| C23C 16/08 | (2006.01) |

(52) U.S. Cl.
CPC ................ C07F 3/06 (2013.01); C23C 16/407 (2013.01); C23C 16/08 (2013.01)
USPC .................... 106/1.29; 556/128; 427/255.14; 427/255.33

(58) Field of Classification Search
USPC ......... 556/128; 427/255.14, 255.33; 106/1.29
See application file for complete search history.

(56) References Cited

PUBLICATIONS

Guerrero et al., Macromolecular Chemistry and Physics, vol. 209, No. 16, pp. 1714-1720 (2008).*

* cited by examiner

*Primary Examiner* — Porfirio Nazario Gonzalez
(74) *Attorney, Agent, or Firm* — McDermott Will & Emery LLP

(57) ABSTRACT

A zinc oxide precursor for use in deposition of a zinc oxide-based thin film contains an alkyl zinc halide having the following formula: R—Zn—X, where R is an alkyl group $C^nH_{2n+1}$, and X is a halogen group. The n is a number ranging from 1 to 4, and the alkyl group is one selected from among a methyl group, an ethyl group, an i-propyl group and a t-butyl group. The halogen group contains one selected from among F, Br, Cl and I. A method of depositing a zinc oxide-based thin film includes loading a substrate into a deposition chamber; and supplying the zinc oxide precursor which contains the above-described alkyl zinc halide and an oxidizer into the deposition chamber and forming a zinc oxide-based thin film on the substrate via chemical vapor deposition. The zinc oxide-based thin film is deposited on the substrate via atmospheric pressure chemical vapor deposition.

6 Claims, 8 Drawing Sheets

FIG. 1

DEZ: Diethyl Zinc
TEB: Tetraethyl Boron
MFC: Mass Flow Controller

US 8,858,694 B2

ZINC OXIDE PRECURSOR CONTAINING ALKYL ZINC HALIDE AND METHOD OF DEPOSITING ZINC OXIDE-BASED THIN FILM USING THE SAME

CROSS REFERENCE TO RELATED APPLICATION

The present application claims priority from Korean Patent Application Number 10-2011-0120424 filed on Nov. 17, 2011, the entire contents of which are incorporated herein for all purposes by this reference.

BACKGROUND OF THE INVENTION

1. Field of the Invention

The present invention relates to a zinc oxide precursor containing an alkyl zinc halide for use in deposition of a zinc oxide-based thin film and a method of depositing a zinc oxide-based thin film using the same.

2. Description of Related Art

Flat panel displays, such as a thin-film transistor liquid crystal display (TFT-LCD), a plasma display panel (PDP), a field emission display (FED), and an organic light-emitting diode (OLED), photovoltaic cells using photoelectric effect, touch screens, or the like require a transparent conducting electrode, i.e. a conductive material which does not block light.

The key material for the transparent conducting electrode is tin (Sn)-doped indium oxide ($In_2O_3$), i.e. indium tin oxide (ITO). ITO is popular as a transparent electrode material since it has superior electric conductivity owing to its low specific resistivity of about 1 or $2\times10^{-4}\Omega m$, has high transmittance in the visible light range, and has excellent chemical stability. However, since the amount of deposits of In, a major component of ITO, is significantly smaller than the amount of deposits of Sn or zinc (Zn), the price of In is high, which is comparable to the price of silver (Ag). In addition, the price fluctuation of In is great, which is also problematic. Accordingly, studies of materials which can substitute for In are actively underway.

Recently, materials in which zinc oxide (ZnO) is doped with a group III cationic metal element, such as aluminum (Al), gallium (Ga), indium (In) or boron (B), or a halogen element, such as fluorine (F) were typically studied as substitute materials of ITO.

According to Korean Patent Application Publication No. 10-2008-0064269, the zinc oxide-based thin film can be deposited on a substrate by physical vapor deposition (PVD), and when sputtering is used in the PVD, a ZnO-based target is used as a target material.

In addition, according to Korean Patent Application Publication No. 10-2006-0125500, the zinc oxide-based thin film can be deposited on the substrate by chemical vapor deposition (CVD), in which diethyl zinc (DEZ), a DEZ octane solution or the like is used for a source material.

FIG. 1 is a view schematically depicting a plasma-enhanced chemical vapor deposition (PECVD) apparatus of the related art which deposits a zinc oxide-base thin film using diethyl zinc (DEZ) or dimethyl zinc (DMZ) as a source material.

FIG. 1 illustrates a PECVD apparatus which deposits undoped ZnO and F— and B-doped ZnO. The PECVD apparatus shown in FIG. 1 forms a reaction composition by combining DEZ or DMZ as a fugitive organic metal zinc compound, Ar or He as a carrier gas, $CO_2$ as an oxidizer, and tetraethyl boron or nitrogen trifluoride ($NF_3$) as a dopant, and blows the reaction composition into a deposition chamber 1, thereby depositing a zinc oxide-based thin film on a substrate 5.

Among reference numerals which have not been described, 2 indicates an upper electrode, 3 indicates a lower electrode, 4 indicates a hole, 6 indicates an opening, 7 indicates a power source, 8, 9, 10, 11, 12 and 13 indicate lines, 14, 15, 16, 17, 18 and 19 indicate mass flow controllers (MFCs), and 20 indicates a thermostat.

FIG. 2 is a view schematically depicting a deposition chamber of the related art which deposits a zinc oxide-based thin film using a solution which was manufactured by dissolving DEZ into an organic solvent as a source material.

A solution that was manufactured by dissolving DMZ or DEZ into an organic solvent (ether, ketone, ester, hydrocarbon or alcohol) is gasified. The gasified solution is supplied into a chemical vapor deposition (CVD) apparatus via a duct 24, and at the same time, an oxidizer gas (oxygen gas, ozone gas, nitrogen oxide gas or water vapor) is supplied into a deposition chamber via a duct 25.

Among reference numerals which have not been described, 21 indicates a substrate, 22 indicates a susceptor, 23 indicates a heater, 26 indicates a rotary shaft, 27 indicates a reactant gas outlet, and 29 indicates a reaction chamber.

However, when DEZ or DMZ is used as in FIG. 1, there are problems in that the vapor pressure is too high, the danger of ignition is significant owing to high reactivity, it is not easy to control the composition of the thin film. In particular, there are disadvantages in that the deposition of the zinc oxide-based thin film using a precursor, such as DEZ or DMZ, must be carried out under low pressure, and that the atmospheric pressure chemical vapor deposition (APCVD) cannot be used.

In addition, although the method of using the precursor, such as DEZ or DMZ, by dissolving it into an organic solvent has an advantage of capable to suppressing natural ignition, the disadvantage is that the yield is poor since the deposition rate is low owing to the low zinc content. Furthermore, since the solvent which has not volatized at a low temperature deposition increases the danger of ignition, this method must be used for only high temperature deposition, which is also disadvantageous.

The information disclosed in the Background of the Invention section is only for better understanding of the background of the invention, and should not be taken as an acknowledgment or any form of suggestion that this information forms a prior art that would already be known to a person skilled in the art.

BRIEF SUMMARY OF THE INVENTION

The present invention has been made keeping in mind the foregoing problems of the related art, and an object of the present invention is to synthesize alkyl zinc halide as an organic material which can substitute for diethyl zinc (DEZ) or dimethyl zinc (DMZ) of the related art and be applied to chemical vapor deposition of a zinc oxide-based thin film.

An object of the present invention is to provide a novel source material which can reduce process-related problems attributable to thermal or chemical instability, has excellent thermal and chemical stability and high vapor pressure, and does not ignite in moisture or in air, so that a superior zinc oxide-based thin film without impurities such as carbon can be deposited by changing only process conditions, such as a reactant gas or a change in deposition temperature.

In particular, an object of the present invention is to enable a zinc oxide-based thin film to be mass-produced via atmospheric pressure vapor deposition, which is suitable to mass production due to a fast deposition rate and high yield.

In an aspect of the present invention, provided is a zinc oxide precursor for use in deposition of a zinc oxide-based thin film. The zinc oxide precursor contains an alkyl zinc halide having the following formula:

where R is an alkyl group $C_nH_{2n+1}$, and X is a halogen group.

In an exemplary embodiment, the n in the alkyl group may be a number ranging from 1 to 4, and the alkyl group may be one selected from the group consisting of a methyl group, an ethyl group, an i-propyl group and a t-butyl group.

In an exemplary embodiment, the halogen group may contain one selected from the group consisting of F, Br, Cl and I.

In another aspect of the present invention, provided is a method of depositing a zinc oxide-based thin film. The method includes the following steps of: loading a substrate into a deposition chamber; and supplying the zinc oxide precursor which contains the above-described alkyl zinc halide and an oxidizer into the deposition chamber and forming a zinc oxide-based thin film on the substrate via chemical vapor deposition.

In an exemplary embodiment, the zinc oxide-based thin film may be deposited on the substrate via atmospheric pressure chemical vapor deposition.

As set forth above, an alkyl zinc halide organic metal compound according to embodiments of the invention can be relatively safely applied to atmospheric pressure chemical vapor deposition (APCVD) since the ignitability of the byproduct produced during the reaction caused by the oxidizer is smaller than the ignitability of an ethane gas or a methane gas which is a precursor byproduct of DEZ or DMZ.

Since the compound does not need to be diluted using a hydrocarbon-based solvent owing to its low ignitability, it is possible to acquire a higher yield based on a fast deposition rate using the precursor having a high zinc content.

The methods and apparatuses of the present invention have other features and advantages which will be apparent from, or are set forth in greater detail in the accompanying drawings, which are incorporated herein, and in the following Detailed Description of the Invention, which together serve to explain certain principles of the present invention.

BRIEF DESCRIPTION OF THE DRAWINGS

FIG. 1 is a view schematically depicting a plasma-enhanced chemical vapor deposition (PECVD) apparatus of the related art which deposits a zinc oxide-base thin film using diethyl zinc (DEZ) or dimethyl zinc (DMZ) as a source material;

DETAILED DESCRIPTION OF THE INVENTION

Figure 2:
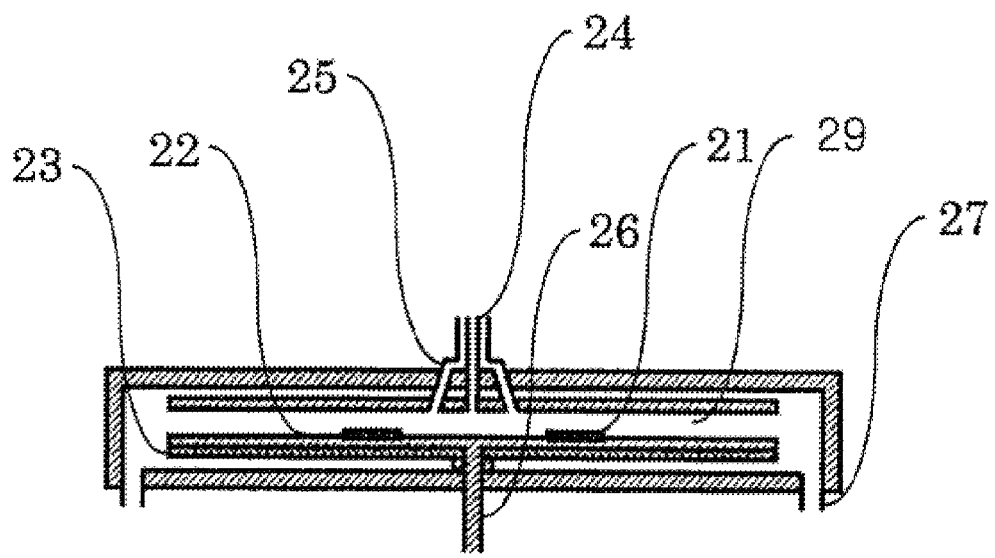
FIG. 2 is a view schematically depicting a deposition chamber of the related art which deposits a zinc oxide-based thin film using a solution which was manufactured by dissolving DEZ into an organic solvent as a source material

Reference will now be made in detail to various embodiments of the present invention, examples of which are illustrated in the accompanying drawings and described below, so that a person having ordinary skill in the art to which the present invention relates can easily put the present invention into practice.

Throughout this document, reference should be made to the drawings, in which the same reference numerals and signs are used throughout the different drawings to designate the same or similar components. In the following description of the present invention, detailed descriptions of known functions and components incorporated herein will be omitted when they may make the subject matter of the present invention unclear.

In the present invention, chemical vapor deposition (CVD) is carried out using alkyl zinc halide which has a composition expressed by Formula 1 below as an organic metal compound that can substitute for a zinc oxide precursor, such as diethyl zinc (DEZ) or dimethyl zinc (DMZ), which has been used in the related art.

 Formula 1

In Formula 1, R indicates an alkyl group $C_nH_{2n+1}$, and X indicates a halogen group.

Figure 3:
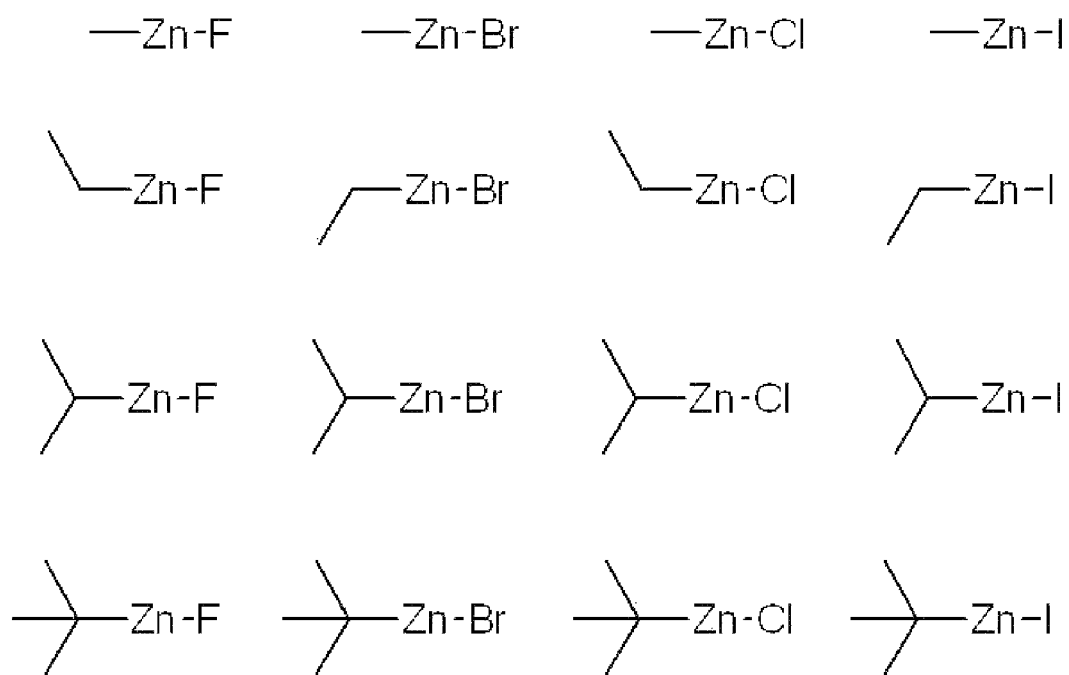
FIG. 3 is a view depicting a variety of alkyl zinc halides according to the invention.

Here, it is preferred that n range from 1 to 4, and that R be one selected from among a methyl group, an ethyl group, an i-propyl group and a t-butyl group. It is preferred that X be one selected from among F, Br, Cl and I. FIG. 3 depicts a variety of alkyl zinc halides according to the invention which has the above-described alkyl group and the above-described halogen group.

When the alkyl zinc halide having Formula 1 is used as a source material, the source material is not required to be diluted using a hydrocarbon-based solvent since it has lower reactivity and ignitability than DEZ. Therefore, it is possible to acquire a higher yield based on a rapid deposition rate attributable to the high zinc content. In addition, since the ignitability of a byproduct produced during the reaction caused by the oxidizer is smaller than the ignitability of an ethane gas, a methane gas or the like, which is an oxidation byproduct of the precursor, such as DEZ or DMZ, it is possible to deposit a zinc oxide-based thin film by relatively safely carrying out the CVD.

Figure 4:
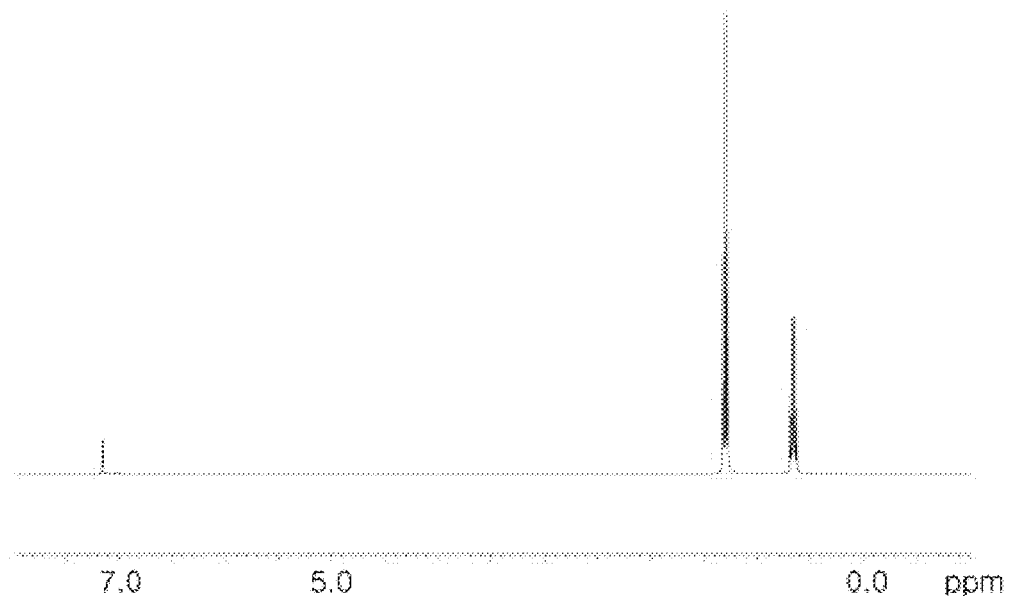
FIG. 4 is a view depicting the result of analyzing ethyl zinc chloride which is manufactured according to an embodiment of the invention.

Among compounds having the composition of Formula 1 above, in particular, a compound in which R has a methyl group or an ethyl group has high vapor pressure. As advantages, it is easy to supply a precursor and control the flow rate of the precursor and is possible to carry out deposition under process conditions of a low temperature. In particular, it is more preferred to use methyl zinc chloride (boiling point 67° C.) and ethyl zinc chloride (boiling point 215° C., shown in FIG. 4) as a source material of the CVD.

It is possible to manufacture alkyl zinc halide by preparing a dispersion solution from zinc halide using an organic solvent in an inert gas atmosphere, and then causing redistribution reaction by adding dialkylzinc which is diluted using an organic solvent into the dispersion solution. It is also possible to manufacture alkyl zinc halide by preparing a dispersion solution from zinc halide using an organic solvent and then causing reduction by adding an alkali metal or an alkaline earth metal into the dispersion solution.

Figure 5:
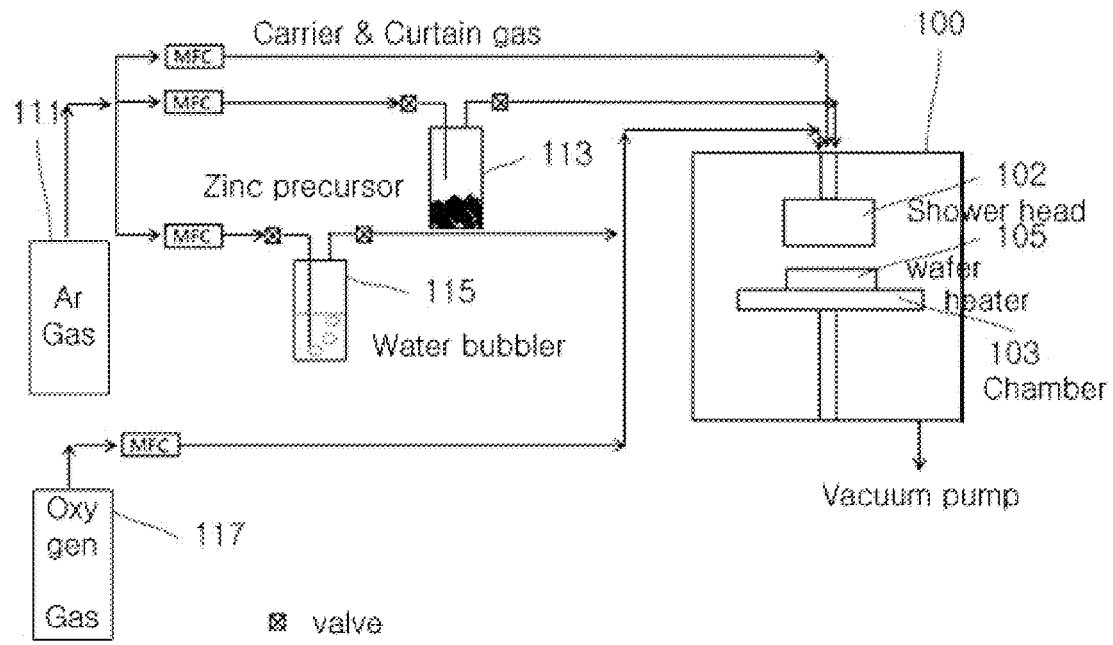
FIG. 5 is a view schematically depicting a chemical vapor deposition (CVD) apparatus according to an embodiment of the invention.

FIG. 5 is a view depicting the schematic structure of a CVD apparatus according to an embodiment of the invention.

Figure 6:
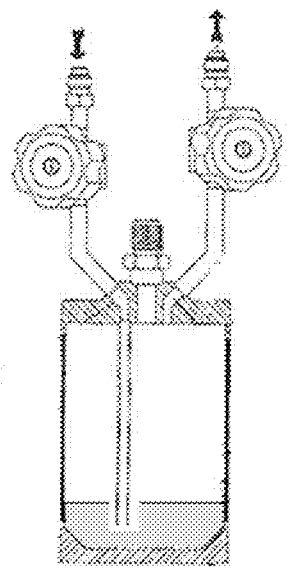
FIG. 6 and FIG. 7 are views schematically depicting examples of the canister shown in FIG. 5.
Figure 7:
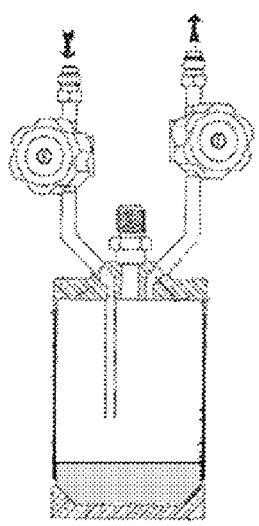

The CVD apparatus may include a canister 113 or a vaporizer which has a dip tube, as shown in FIG. 6, or a tube, as shown in FIG. 7, in order to gasify alkyl zinc halide. Here, i) a gas is supplied into the canister 113 via the dip tube or the tube from a gas supply 111 in order to help alkyl zinc halide be gasified, or ii) alkyl zinc halide in a gas state which was produced by generating only vapor without supplying a gas is supplied along with a carrier gas.

Here, oxidizer gases (oxygen gas, ozone gas, nitrogen oxide gas, water vapor or alcohol vapor) from oxidizer supplies 115 and 117 are supplied together into a deposition chamber 100.

An upper electrode 102 has the shape of a shower head. The shower head refers to a chamber, a plenum or other structures having a plurality of holes through which a precursor or the like is ejected into the deposition chamber 100.

The substrate 105 may be implemented as a silicon (Si) substrate, a sapphire substrate, a ceramic substrate, a glass substrate, a metal oxide substrate, a metal substrate or the like. In order to efficiently form a zinc oxide-based thin film, the temperature of the substrate can be set between 100° C. and 400° C., and preferably, between 250° C. and 350° C. It is therefore possible to form a reproducible zinc oxide-based thin film by depositing the supplied organic zinc compound onto the substrate, which is heated to the above-defined temperature, via the CVD.

In order to produce a zinc oxide-based thin film which is doped with a dopant, for example, gallium (Ga), it is possible to introduce the dopant into the deposition chamber 100 so that the dopant can also be deposited, or carry out doping in the subsequent process.

EXAMPLE 1

A glass substrate was set to a heater of a deposition chamber of a CVD apparatus, and the degree of vacuum inside the deposition chamber was set $1.0 \times 10^{-6}$ torr. Afterwards, the temperature inside a canister was set 50° C., and the temperature of the glass substrate was maintained at 300° C. A zinc oxide-based thin film was formed on the glass substrate for several minutes by supplying a gas at a flow rate of 20 sccm/min to an ethyl zinc chloride precursor using a gas flow rate controller in order to help a source material become gasified, supplying argon (Ar) gas at a flow rate of 50 sccm/min through a carrier gas supply line which was heated to 80° C., and supplying oxygen ($O_2$) gas at a flow rate of 13 sccm/min.

Figure 8:
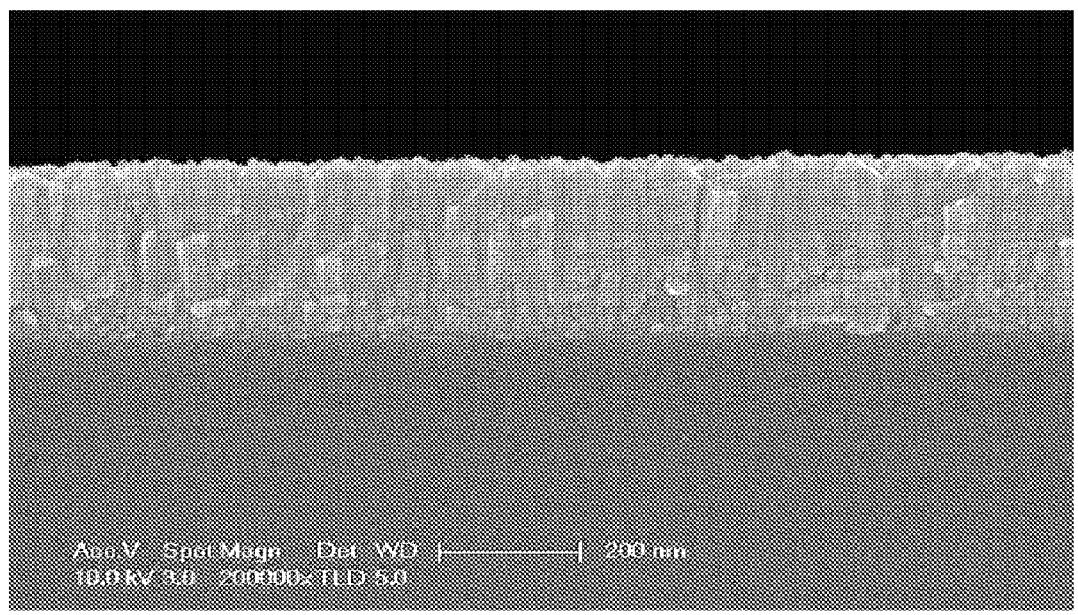
FIG. 8 to FIG. 10 are views depicting the results of analyzing a zinc oxide-based thin film which was deposited according to Example 1.
Figure 9:
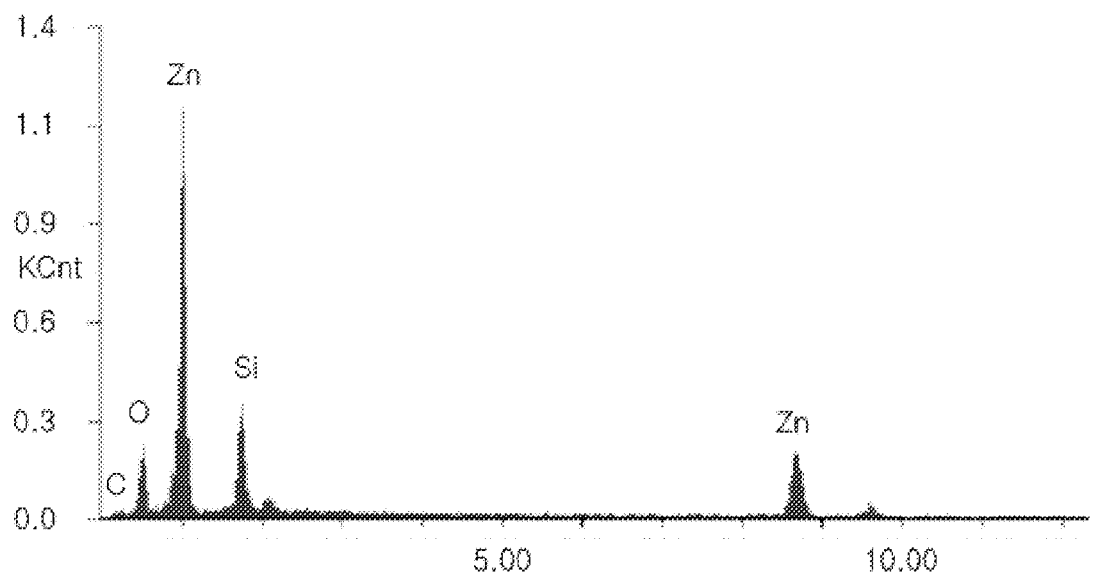
Figure 10:
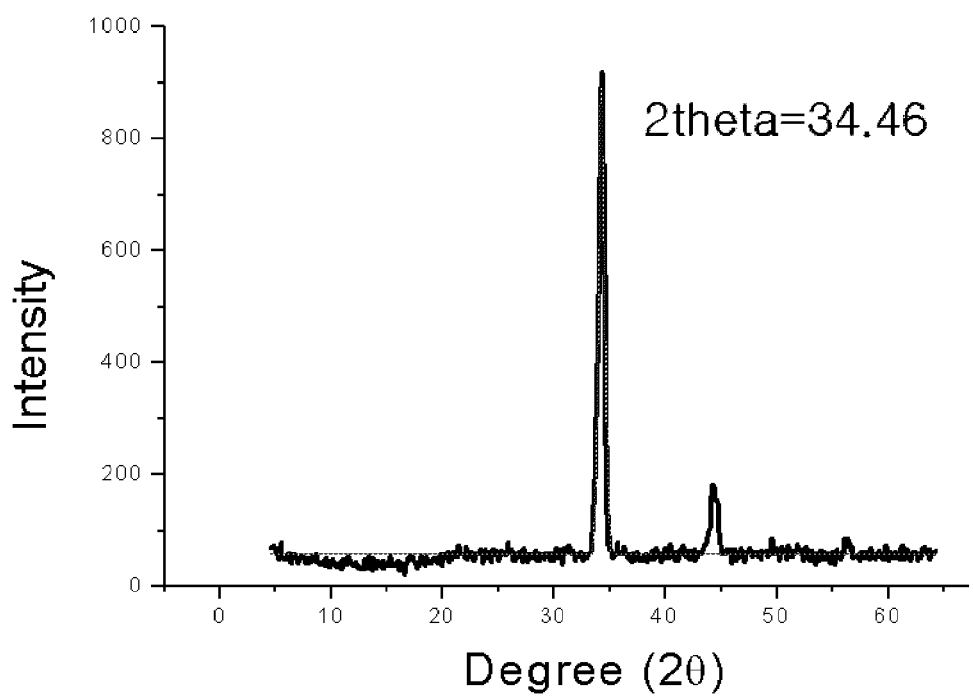

When the zinc oxide-based thin film produced above was analyzed using a scanning electron microscope (SEM), crystallinity which grew in the direction of the c-axis of a columnar structure having a thin-film thickness of 344 nm appeared (see FIG. 8 and FIG. 9). In addition, as the result of X-ray diffraction analysis, a (002) crystal face in the c-axis direction appeared in vicinity of $2\theta=34.4$ (degrees) (see FIG. 10). Furthermore, as the result of analysis using a sheet resistance tester, a resistance of $6.686 \times 10^1 \Omega/sq$ (a specific resistance of $2.3 \times 10^{-4} \Omega cm$) was obtained. In addition, as the result of analysis using an infrared (IR) spectrometer, it was observed that transmittance was 80% or greater in the visible light range.

Accordingly, it was possible to produce the transparent conductive zinc oxide-based thin film which has the (002) crystal face in the c-axis direction, in which carrier mobility is excellent, and has high light transmittance and a low resistance.

EXAMPLE 2

A glass substrate was set to a heater of a deposition chamber of a CVD apparatus, and a CVD apparatus was set to atmospheric pressure. Afterwards, the temperature inside a canister was set 50° C., and the temperature of the glass substrate was maintained at 350° C. A zinc oxide-based thin film was formed on the glass substrate for several minutes by supplying a gas at a flow rate of 500 sccm/min to an ethyl zinc chloride precursor using a gas flow rate controller in order to help a source material be gasified, supplying Ar gas at a flow rate of 200 sccm/min through a carrier gas supply line which was heated to 80° C., and supplying $O_2$ gas at a flow rate of 130 sccm/min.

Figure 11:
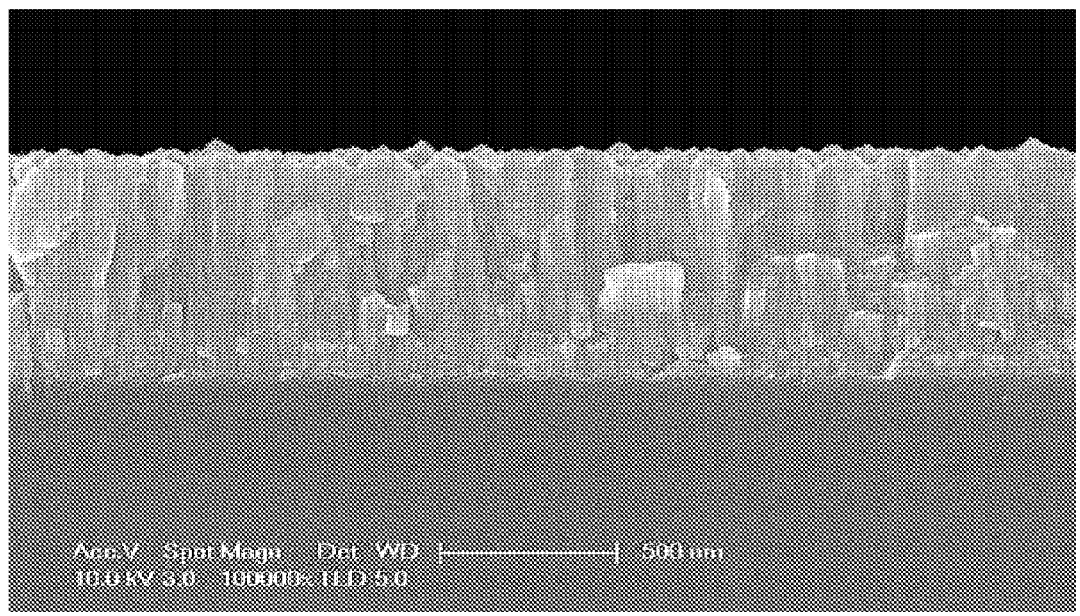
FIG. 11 to FIG. 13 are views depicting the results of analyzing a zinc oxide-based thin film which was deposited according to Example 2.
Figure 12:
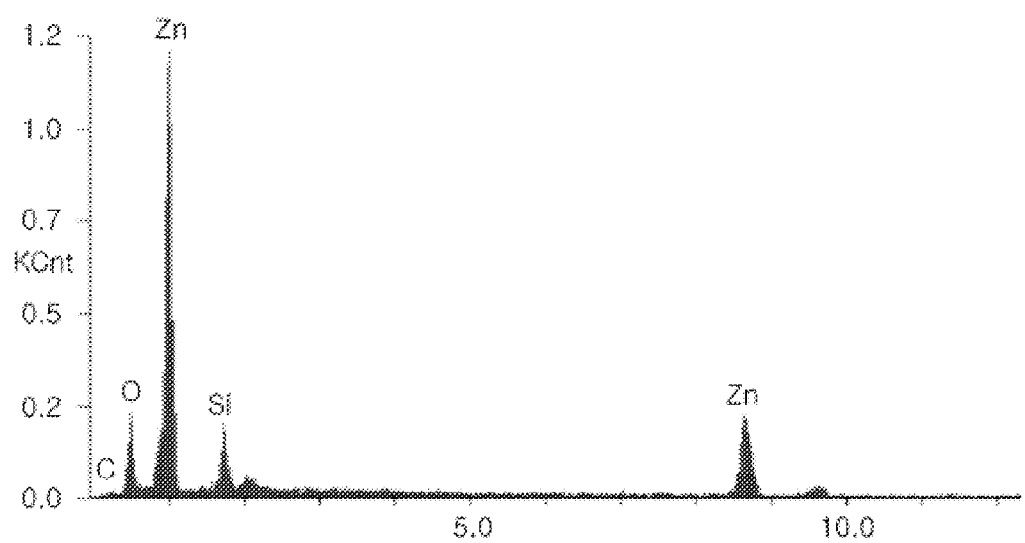
Figure 13:
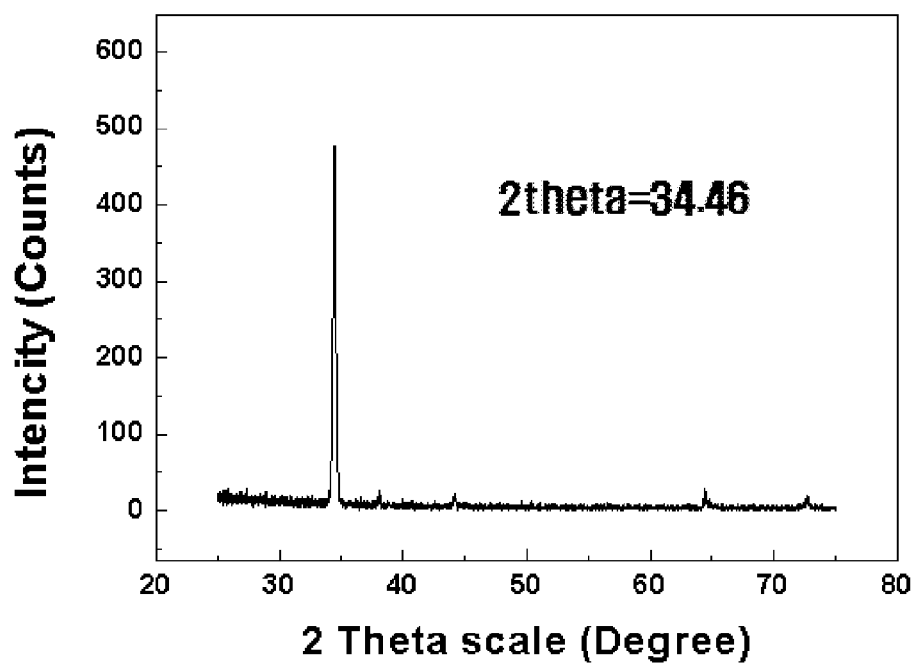

When the zinc oxide-based thin film produced above was analyzed using an SEM, crystallinity which grew in the c-axis direction of a columnar structure having a thin-film thickness of 875 nm appeared (see FIG. 11 and FIG. 12). In addition, as the result of X-ray diffraction analysis, a (002) crystal face in the c-axis direction appeared in vicinity of $2\theta=34.4$ (degrees) (see FIG. 13). Furthermore, as the result of analysis using a sheet resistance tester, a resistance of $8.0 \times 10^1 \Omega/sq$ (a specific resistance of $7 \times 10^{-4} \Omega cm$) was obtained. In addition, as the result of analysis using an infrared (IR) spectrometer, it was observed that transmittance was 80% or greater in the visible light range.

Accordingly, it was possible to produce the transparent conductive zinc oxide-based thin film which has the (002) crystal face in the c-axis direction, in which carrier mobility is excellent, and has high light transmittance and a low resistance.

The foregoing descriptions of specific exemplary embodiments of the present invention have been presented with respect to the certain embodiments and drawings. They are not intended to be exhaustive or to limit the invention to the precise forms disclosed, and obviously many modifications and variations are possible for a person having ordinary skill in the art in light of the above teachings.

It is intended therefore that the scope of the invention not be limited to the foregoing embodiments, but be defined by the Claims appended hereto and their equivalents.

What is claimed is:

1. A zinc oxide precursor composition for use in deposition of a zinc oxide-based thin film, comprising:
   an alkyl zinc halide having the following formula:

   R—Zn—X, where R is an alkyl group $C_nH_{2n+1}$, and X is a halogen group;
   a carrier gas; and
   an oxidizing gas.

2. The zinc oxide precursor composition of claim 1, wherein the n in the alkyl group is a number ranging from 1 to 4.

3. The zinc oxide precursor composition of claim 2, wherein the alkyl group comprises one selected from the group consisting of a methyl group, an ethyl group, an i-propyl group and a t-butyl group.

4. The zinc oxide precursor composition of claim 1, wherein the halogen group comprises one selected from the group consisting of F, Br, Cl and I.

5. The zinc oxide precursor composition of claim 1, wherein the alkyl group comprises a methyl group or an ethyl group, and the halogen group comprises Cl.

6. The zinc oxide precursor composition of claim 1, comprising a zinc oxide precursor for use in atmospheric pressure chemical vapor deposition.

* * * * *